(12) United States Patent
Thrasher et al.

(10) Patent No.: US 10,190,959 B2
(45) Date of Patent: Jan. 29, 2019

(54) SORTING FLOW CYTOMETER

(71) Applicant: BECKMAN COULTER, INC., Brea, CA (US)

(72) Inventors: Thomas L. Thrasher, Fort Collins, CO (US); Bruce G. Bailey, Fort Collins, CO (US); Eric Von Seggern, Johnstown, CO (US); Jeffrey W. Degeal, Loveland, CO (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 14/377,623

(22) PCT Filed: Feb. 8, 2013

(86) PCT No.: PCT/US2013/025308
§ 371 (c)(1),
(2) Date: Aug. 8, 2014

(87) PCT Pub. No.: WO2013/119924
PCT Pub. Date: Aug. 15, 2013

(65) Prior Publication Data
US 2015/0050688 A1 Feb. 19, 2015

Related U.S. Application Data

(60) Provisional application No. 61/597,022, filed on Feb. 9, 2012.

(51) Int. Cl.
G05B 17/02 (2006.01)
G01N 15/14 (2006.01)
(Continued)

(52) U.S. Cl.
CPC ..... *G01N 15/1404* (2013.01); *G01N 15/1425* (2013.01); *G01N 35/08* (2013.01);
(Continued)

(58) Field of Classification Search
USPC ............ 422/73, 62–63, 93, 509; 436/10, 43; 700/29, 266; 702/21
See application file for complete search history.

(56) References Cited

U.S. PATENT DOCUMENTS 4,347,935 A    9/1982  Merrill
4,981,580 A *  1/1991  Auer ...................... B07C 5/342
                                                   209/3.1
(Continued)

FOREIGN PATENT DOCUMENTS

CN    101675334 A    3/2010
CN    101995374 A    3/2011
(Continued)

OTHER PUBLICATIONS

International Search Report for International Application No. PCT/US2013/025308 dated Jun. 27, 2013 (3 pages).

*Primary Examiner* — Dean Kwak
(74) *Attorney, Agent, or Firm* — Merchant & Gould P.C.

(57) ABSTRACT

A sorting flow cytometer identifies an undesirable drop charge sequence that is preassigned to adjacent drops before the drops have separated from a fluid stream. An example of an undesirable drop charge sequence is a sequence of adjacent drops that are charged with sufficiently high opposing charges that, after the drops are formed, would result in merging of the adjacent drops. The sorting flow cytometer adjusts the assignment of drop charges to avoid the undesired drop charge sequence.

7 Claims, 12 Drawing Sheets

(51) Int. Cl.
*G01N 35/08* (2006.01)
*G01N 15/10* (2006.01)

(52) U.S. Cl.
CPC ............ *G01N 2015/1043* (2013.01); *G01N 2015/149* (2013.01); *G01N 2015/1481* (2013.01)

(56) References Cited

U.S. PATENT DOCUMENTS

| | | | |
|---|---|---|---|
| 5,483,469 A | 1/1996 | Van den Engh et al. | |
| 5,550,058 A | 8/1996 | Corio et al. | |
| 5,617,911 A | 8/1997 | Sterett et al. | |
| 6,079,836 A * | 6/2000 | Burr | G01N 15/1404 356/335 |
| 6,589,792 B1 | 7/2003 | Malachowski | |
| 2003/0211009 A1* | 11/2003 | Buchanan | G01N 15/1456 422/63 |
| 2005/0019949 A1 | 1/2005 | Hall et al. | |
| 2008/0255705 A1* | 10/2008 | Degeal | B07C 5/342 700/273 |
| 2008/0293146 A1* | 11/2008 | Frazier | G01N 15/1404 436/63 |
| 2009/0287356 A1* | 11/2009 | Dunne | G01N 15/1427 700/282 |
| 2011/0177547 A1 | 7/2011 | Zheng et al. | |
| 2012/0202237 A1* | 8/2012 | Sedoglavich | G01N 15/1404 435/29 |
| 2014/0212917 A1* | 7/2014 | Durack | G01N 15/1427 435/34 |

FOREIGN PATENT DOCUMENTS

| | | |
|---|---|---|
| JP | 2002505422 A | 2/2002 |
| JP | 2011237201 A | 11/2011 |
| WO | 2009078307 A1 | 6/2009 |

* cited by examiner

FIG. 9

| BUFFER – PRELIMINARY SORT DECISIONS | |
|---|---|
| POSITION (N=NEXT) | CHARGE TO BE APPLIED |
| N+4 | +1 |
| N+3 | -3 |
| N+2 | +2 |
| N+1 | -3 |
| N | -1 |

330

UNDESIRED SORT SEQUENCE: N+3, N+2, N+1

| BUFFER – PRELIMINARY SORT DECISIONS WITH PRIORITY DATA | | |
|---|---|---|
| POSITION (N=NEXT) | CHARGE TO BE APPLIED | PRIORITY (1=HIGH) |
| N+4 | +1 | 3 |
| N+3 | -3 | 1 ← HIGHER PRIORITY |
| N+2 | +2 | 2 ← LOWER PRIORITY |
| N+1 | -3 | 1 ← HIGHER PRIORITY |
| N | -1 | 3 |

330'

UNDESIRED SORT SEQUENCE { N+3, N+2, N+1 }

| BUFFER – FINAL SORT DECISIONS ||
|---|---|
| POSITION (N=NEXT) | CHARGE TO BE APPLIED |
| N+4 | +1 |
| N+3 | -3 |
| N+2 | NONE ← ABORT SORTING FOR THIS DROP |
| N+1 | -3 |
| N | -1 |

362

SORTING FLOW CYTOMETER

This application is being filed on 8 Aug. 2014, as a US National Stage of PCT International Patent application No. PCT/US2013/025308, filed 8 Feb. 2013 and claims priority to U.S. Patent Application Ser. No. 61/597,022 filed on 9 Feb. 2012, the disclosure of which is incorporated herein by reference in its entirety.

BACKGROUND

A flow cytometer is useful for identifying particles and characteristics of particles contained within a fluid. The fluid is typically passed through a small nozzle that generates a narrow fluid stream. A laser beam illuminates the particles in the fluid stream as they pass. Detectors are positioned to detect light transmission and scatter. This information is then used by the flow cytometer to identify the particles and characteristics of the particles in the fluid.

A sorting flow cytometer uses information about the particles to sort the particles into different containers. To do so, the fluid stream is divided into a series of individual drops containing one or more of the particles. Each drop containing one or more particles to be sorted is given an electrical charge based on the particle characteristics. The drops are then passed between oppositely charged deflection plates. Positively charged drops are displaced toward the negatively charged plate, while negatively charged drops are displaced toward the positively charged plate. The larger the charge, the greater the displacement of the drop. The drops are sorted into multiple different containers arranged below and between the plates.

SUMMARY

In general terms, this disclosure is directed to a sorting flow cytometer. In one possible configuration and by non-limiting example, the sorting flow cytometer identifies an undesirable preassigned drop charge sequence, such as a drop charge sequence that would result in merging of adjacent drops if the drop charges are applied to adjacent drops. The sorting flow cytometer adjusts the charges to be applied to the drops to avoid the formation of the undesired drop charge sequence.

One aspect is a method of operating a sorting flow cytometer, the method comprising: identifying, with a computing device, an undesired drop charge sequence assigned to two or more adjacent drops prior to the separation of the drops from a fluid stream; and aborting a sort operation for at least one of the drops in the fluid stream to avoid the undesired drop charge sequence Another aspect is a sorting flow cytometer comprising: a fluid nozzle, a laser, a computing device, sort control electronics, and deflection plates. The fluid nozzle is configured to receive a fluid input and generate a fluid stream along a fluid path. The laser is configured to generate a laser beam and positioned to direct the laser beam at the fluid stream. The acquisition electronics including a sensor analyzer arranged and configured to detect light from the laser after the laser beam has intersected the fluid stream. The computing device receives event data from the acquisition electronics and generates a preliminary sort decisions assigned to segments of the fluid stream; identifies an undesired drop charge sequence assigned to at least two adjacent segments of the fluid stream; generates final sort decisions by modifying the preliminary sort decisions to abort a sorting operation for at least one of the fluid segments; and generates a sort control signal according to the final sort decisions. The sort control electronics receive the sort control signal and selectively apply charges to the fluid stream. The deflection plates are arranged adjacent the fluid path to sort drops associated with the fluid segments from the fluid stream into a plurality of containers.

A further aspect is a computer readable medium storing program instructions, wherein the program instructions, when executed by a processing device, causing the processing device to identify an undesired drop charge sequence assigned to at least two adjacent drops prior to the separation of the drops from a fluid stream; and abort a sort operation for at least one of the drops in the fluid stream to avoid the undesired drop charge sequence.

Another aspect is a method of operating a sorting flow cytometer, the method comprising: characterizing particles associated with a first drop and a second drop along a fluid path; preassigning a charge to the first drop and the second drop based on the characterization of the one or more particles associated with each drop; and selectively not applying the preassigned charge to one of the first drop and the second drop based at least in part on the magnitude of the preassigned charge of the first drop and the second drop.

A further aspect is a method of operating a sorting flow cytometer, the method comprising: characterizing a first particle and a second particle in a fluid stream; assigning a preliminary charge to the first particle and the second particle based on the characterization of the first particle and the second particle, respectively; assigning final charges to the first particle and the second particle based on the preliminary charges assigned to the first particle and the second particle; and sorting the first particle and the second particle based on the assigned final charges.

Yet another aspect is a method of operating a sorting flow cytometer, the method comprising: a) characterizing a first particle; b) assigning a deflection value to the first particle; c) characterizing a second particle; d) assigning a deflection value to the second particle; e) changing the assigned deflection value of one of the first particle and the second particle if the deflection value of the first particle exceeds a maximum deflection value and the deflection value of the second particle exceeds a maximum opposing deflection value; and f) sorting the first particle and the second particle based on the assigned deflection values.

Another aspect is a method of operating a sorting flow cytometer, the method comprising: a) characterizing a first particle; b) assigning a charge and a priority to the first particle; c) characterizing a second particle; d) assigning a charge and a priority to the second particle; e) changing the charge assigned to the one of the first particle and the second particle having the lower assigned priority, wherein the change is based on the charges assigned to the first particle and the second particle; and f) sorting the first particle and the second particle based on the charges assigned to the first particle and the second particle after operation (e).

An additional aspect is a method of operating a sorting flow cytometer, the method comprising: characterizing particles associated with three consecutive drops of the fluid stream, the three consecutive drops including a middle drop between a first drop and a third drop; preassigning a charge to each of the three consecutive drops based on the characterization of the particle associated with each drop; and assigning to at least one of the three consecutive drops a charge that is different than the corresponding preassigned charge if the preassigned charge of the middle drop is greater than a predetermined maximum value and the preassigned charge of the first drop or the third drop is greater than a predetermined maximum opposing value.

Another aspect is a sorting flow cytometer system comprising a contaminant hood, and a sorting flow cytometer. The sorting flow cytometer comprises: a fluid nozzle, a laser, a computing device, sort control electronics, and deflection plates. The fluid nozzle is configured to receive a fluid input and generate a fluid stream along a fluid path. The laser is configured to generate a laser beam and positioned to direct the laser beam at the fluid stream. The acquisition electronics include a sensor analyzer arranged adjacent the fluid beam to detect light from the laser after the laser beam has intersected the fluid stream. The computing device receives event data from the acquisition electronics and generates a preliminary sort decisions assigned to segments of the fluid stream; identifies an undesired drop charge sequence assigned to at least two adjacent segments of the fluid stream; generates final sort decisions by modifying the preliminary sort decisions to abort a sorting operation for at least one of the fluid segments; and generates a sort control signal according to the final sort decisions. The sort control electronics receive the sort control signal and selectively apply charges to the fluid stream. The deflection plates are arranged adjacent the fluid path to sort drops associated with the fluid segments from the fluid stream into a plurality of containers.

BRIEF DESCRIPTION OF THE DRAWINGS

FIG. 9 is a schematic block diagram illustrating an example buffer containing preliminary sort decisions.

FIG. 11 is a schematic block diagram illustrating another example buffer, including drop priority data.

FIG. 12 is a schematic block diagram illustrating an example buffer storing final sorting decisions.

DETAILED DESCRIPTION

Figure 1:
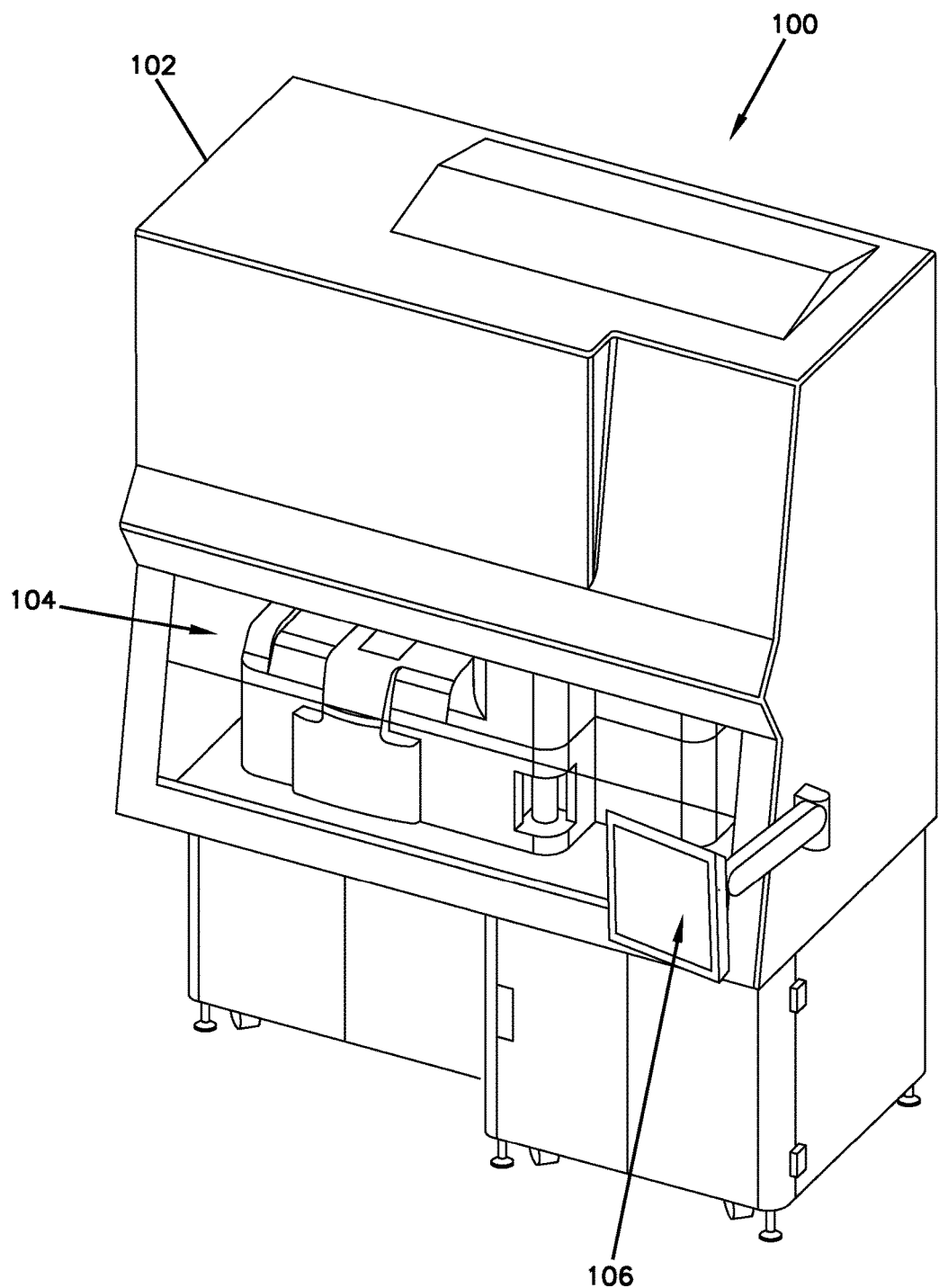
FIG. 1 is a perspective view of an example sorting flow cytometer system including a flow cytometer.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

When performing a sort operation with a sorting flow cytometer, there is the possibility that, prior to sorting, two adjacent drops can have a sufficiently large charge differential that they will be drawn toward each other and merge into a single drop. The resulting drop has a net charge that is the sum of the two individual charges, which is sufficiently different than either of the individual charges, and results in sorting the drop into an unintended location.

The present disclosure describes an approach to solving problems of missorting of particles and contamination of particles during the operation of a sorting flow cytometer by reducing or eliminating the possibility of two oppositely charged drops merging into a single drop prior to sorting.

FIG. 1 is a perspective view of an example sorting flow cytometer system 100. In this example, the sorting flow cytometer system 100 includes a containment hood 102 and a sorting flow cytometer 104. The sorting flow cytometer 104 also includes a display 106 in some embodiments.

In some embodiments, the sorting flow cytometer 104 is arranged within a containment hood 102. The containment hood typically operates to contain particles that may be within a sample to a predetermined region, by maintaining a laminar airflow within the containment hood 102. For example, if the sample contains biological particles, the containment hood 102 operates to contain the particles to the space within the containment hood 102, and out through a controlled exhaust path. In some embodiments filters are used to remove the particles from the air in the exhaust path. An example of a suitable containment hood is the SterilGARD®III 503a Advance, Class II, Type A2 Biological Safety Cabinet with vertical flow available from the Baker Company in Sanford, Me. The dimensions of the cabinet can be expanded or contracted as necessary to properly enclose the sorting flow cytometer 104 therein.

Figure 2:
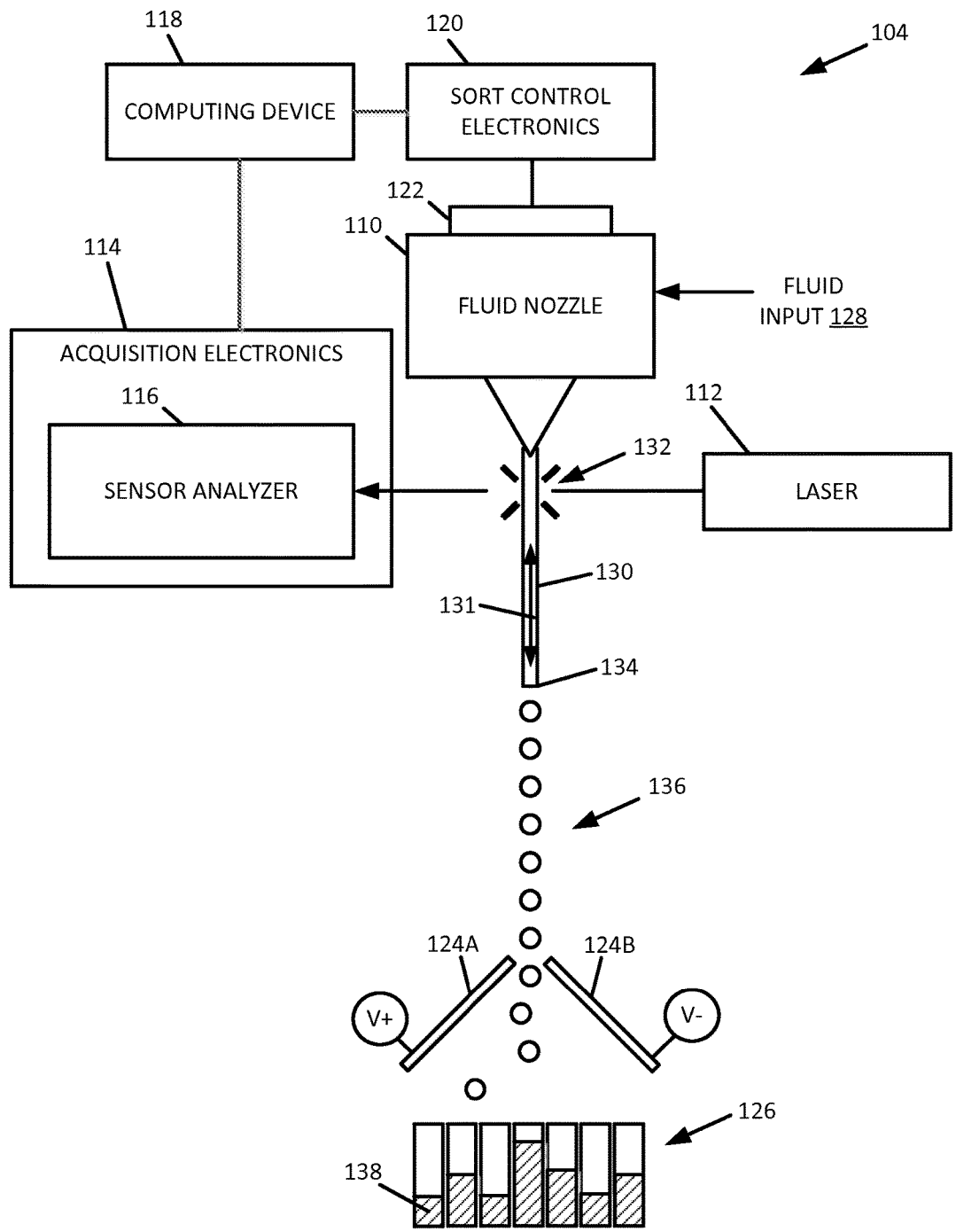
FIG. 2 is a schematic block diagram of the example sorting flow cytometer shown in FIG. 1.

The sorting flow cytometer 104 is a device configured to evaluate the contents of a fluid, and to sort the contents into multiple different containers, based on detected characteristics. (An example of the sorting flow cytometer is illustrated in FIG. 2.)

In some embodiments, the sorting flow cytometer 104 described herein can sort the contents of a fluid with exceptional purity (e.g., greater than 99%), such as by ensuring that drops selected for sorting are appropriately directed into the proper containers.

In some embodiments, a display 106 of the sorting flow cytometer 104 is mounted outside of the containment hood 102. In this example, a bracket is fastened to a side of the containment hood 102. An articulating arm is mounted to the bracket, which operates to support the display 106. The articulating arm pivots in one or more dimensions to permit the display 106 to be repositioned by the operator at a desired location.

Although the sorting flow cytometer 104 is shown positioned within the containment hood 102, some embodiments do not include a containment hood 102.

FIG. 2 is a schematic block diagram of an example sorting flow cytometer 104. In this example, the sorting flow cytometer 104 includes a fluid nozzle 110, a laser 112, acquisition electronics 114 (including a sensor analyzer 116), a computing device 118, sort control electronics 120, an oscillator 122, deflection plates 124, and containers 126. Additional features illustrated in FIG. 2 include a fluid input 128, fluid stream 130, a laser illumination point 132, a drop break off point 134, drops 136, and sorted fluids 138.

The fluid input is provided to the fluid nozzle 110, which generates a narrow fluid stream 130 along a fluid path 131. The width of the fluid stream 130 is approximately the same as the width of the fluid nozzle output port. In some embodiments, the fluid nozzle 110 is removable and can be replaced with other nozzles having different sized output ports. For example, the output ports can be in a range from about 50 micrometers to about 200 micrometers, and in some embodiments between about 70 micrometers and about 100 micrometers.

The laser 112 generates a laser beam that is directed at the fluid stream 130, to illuminate the fluid stream 130 at the laser illumination point 132.

Acquisition electronics 114, such as including a sensor analyzer 116, operate to detect particles in the fluid stream 130 and identify characteristics of the particles. In some embodiments, the sensor analyzer 116 detects light scattering (including forward scatter and side scatter) and fluorescence, and uses this information to identify the presence of particles in the fluid stream and to identify characteristics of the particles. When a particle is detected, event data is generated (as shown in FIG. 3) which is provided to the computing device 118.

Although at the sensor analyzer 116 can be physically positioned directly adjacent to the fluid stream 130, another possible embodiment includes one or more light transmission devices, such as fiber optics, to transmit the light to sensors positioned away from the fluid stream 130.

Figure 3:
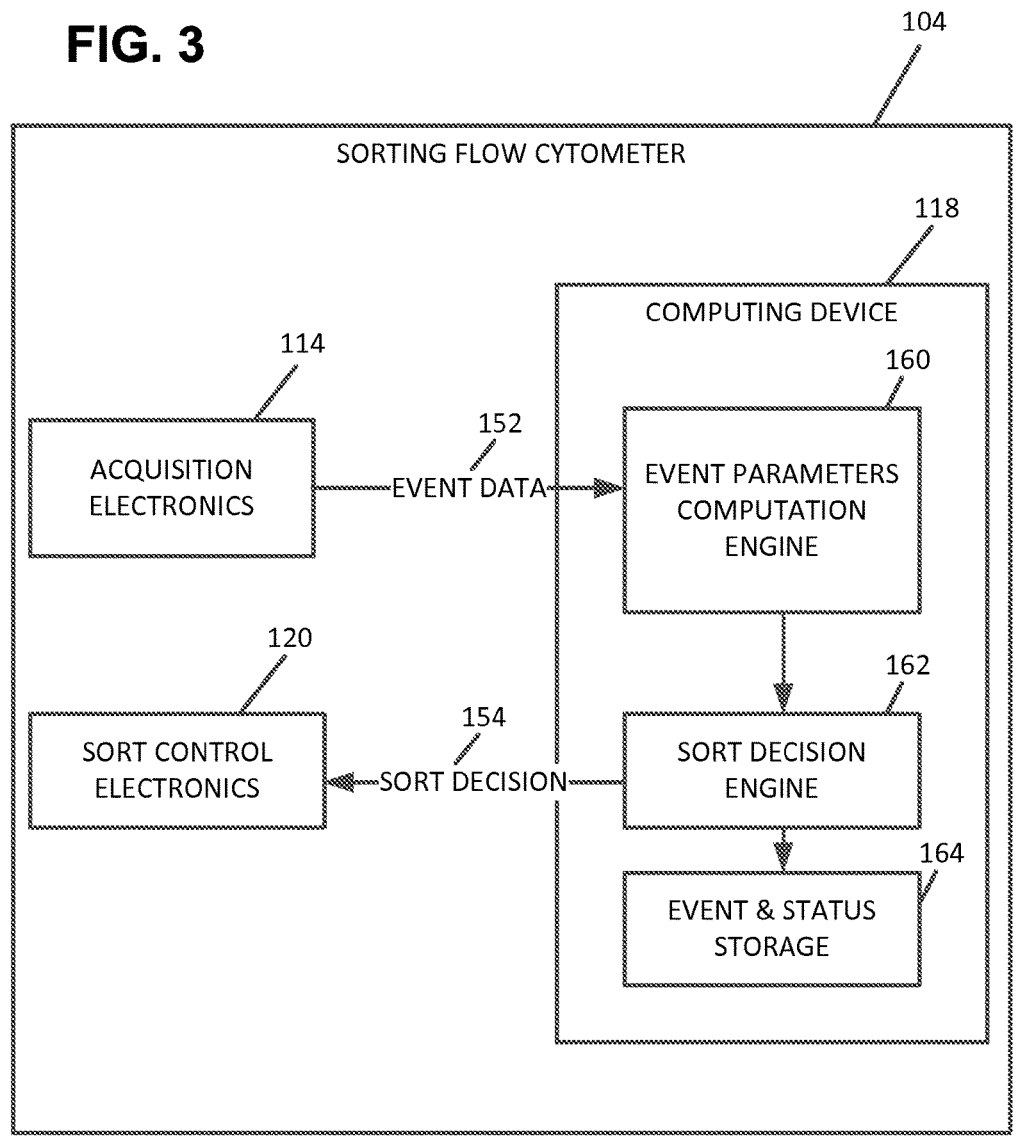
FIG. 3 is a schematic block diagram illustrating additional aspects of the sorting flow cytometer shown in FIG. 2.

The computing device 118 receives the event data and generates a sort control signal based on the raw data, such as illustrated in FIG. 3.

The computing device 118 can be one or more computing devices, and each of the computing devices can include one or more processing devices. Multiple computing devices can be in data communication across a communication bus or a data communication network, for example. The one or more computing devices are referred to herein as "the computing device." An example of a suitable computing device 118 is illustrated and described in more detail herein with reference to FIG. 4.

Sort control electronics 120 receive the sort control signals from the computing device 118 and apply appropriate charges to the fluid stream 130 based on the sort control signals.

The oscillator 122 generates a vibration at a desired frequency, which vibrates the fluid stream 130. The vibrations in the fluid stream 130 cause drops 136 to break off from the fluid stream 130 at regular intervals. The drops 136 then proceed along the fluid path 131.

When the sort control signals indicate that a drop is to be sorted, the sort control electronics 120 apply an appropriate voltage to the fluid stream just before the drop 136 separates from the fluid stream at the drop break off point 134. The voltage creates a physical transformation of the fluid stream by adding or removing electrons from the fluid stream, which is both measurable and detectable on the fluid stream, and the subsequently formed drop 136. When the drop 136 separates, the charge applied to the fluid stream remains on the drop. The sort control electronics can then apply an appropriate charge to the fluid stream 130 for the next drop, based on the sort control signals. If the computing device determines that the fluid for a particular drop does not need to be sorted, the sort control electronics 120 do not apply a charge to the fluid stream before the drop reaches the drop break off point 134.

The drops 136 then pass between charged deflection plates 124. Each of the plates is electrically connected to voltage sources of opposite polarities (e.g., +/−4000V). The voltage sources supply opposing charges of each of the deflection plates 124, which generates an electric field between the deflection plates 124.

As the drops 136 pass between the deflection plates 124, drops 136 that have been given a charge are drawn toward the deflection plate 124 having the opposite polarity. For example, a positively charged drop 136 is drawn toward the negatively charged deflection plate 124b, while a negatively charged drop 136 is drawn toward the positively charged deflection plate 124a. Drops 136 for which a charge is not applied, pass straight through without deflection.

In addition to deflecting drops toward one side or the other, the magnitude of the charge applied to a drop can be varied by the sort control electronics 120 to adjust the degree of displacement. The greater the magnitude of the charge applied to a drop 136, the greater the displacement of the drop 136 toward the oppositely charged deflection plate 124. As a result, drops 136 can be sorted into multiple different containers 126, where they are collected for subsequent use.

In this example, the sorting flow cytometer 104 includes six containers 126, (not including a central waste path or container for unsorted drops). A sorting flow cytometer 104 having six containers can be referred to as a six-way sorting flow cytometer. Other embodiments can include other quantities of containers 126, such as two, four, six, eight, or more.

FIG. 3 is a schematic block diagram illustrating additional aspects of the sorting flow cytometer 104, shown in FIG. 2. In this example, the sorting flow cytometer 104 includes acquisition electronics 114, computing device 118, sort control electronics 120. The computing device includes event parameters computation engine 160, sort decision engine 162, and event and status storage 164. The acquisition electronics 114 provide event data 152 to the computing device 118, and the computing device 118 provides a sort control signal 154 to sort control electronics 120.

The acquisition electronics 114 receive light from the laser 112 (as shown in FIG. 2) after passing through the fluid stream 130 at the laser illumination point, and evaluate the light to detect particles in the fluid stream 130 and identify characteristics of the particles. The acquisition electronics 114 generate event data 152 and supply the event data 152 to the computing device 118.

The computing device 118 includes an event parameters computation engine 160, sort decision engine 162, and event and status storage 164.

The event parameters computation engine 160 receives the event data 152 from the acquisition electronics 114. In some embodiments, the event parameters computation engine 160 also receives sort logic definitions from a user, or retrieves the definitions from a computer-readable storage device. The sort logic definitions contain an arbitrary user-defined equation of the intermediate calculations and the final sort logic equations desired to sort the particles found in the fluid stream. The event parameters computation engine 160 calculates parameter values for parameters in the sort logic definition that are calculated based on the event data 152. Calculated parameters may be based on event data 152 sent by the acquisition electronics 114, constant values entered by the user or stored as standards in a computer-readable storage device, and/or other calculated values.

Once the event parameters computation engine 160 calculates all computed parameter values, the event data 152 and computed parameters for each event are sent to the sort decision engine 162. The sort decision engine 162 plugs the event data and computed parameter values into the sort logic definitions, for example. In some embodiments, the sort logic definitions contain a logic definition, for example, a Boolean logic definition, that identifies the desired sorting of particles.

The sort decision engine 162 evaluates the sort logic definitions, addresses sort ambiguities by selecting a single container 126 (shown in FIG. 2) to receive each encountered event (such as when multiple particles are contained within the drop, which would preferably be sorted into different containers), makes sort decisions, and creates the sort control signal 154 based on the sort decisions. In some embodiments, the sort decision engine 162 first generates a preliminary sort decision based on the identified content of a drop. The preliminary sort decision identifies the container 126 to which the drop should be assigned based at least in part on the sort logic definitions.

The preliminary sort decision comprises a preliminary electrical charge assigned to the drop to direct the drop into the identified container 126. The electrical charge assigned to the drop can be positive, negative, or neutral, where a neutral charge is a charge that causes the drop to travel undeflected along the fluid path 131 as it passes between charged deflection plates 124, such that, for example, it is directed into the centrally positioned container.

Preassigning a charge involves assigning the charge in a preliminary sort decision to a portion of the fluid stream that is predicted to subsequently form an individual drop. The preliminary sort decision is made before generating a final sort decision, where the magnitude of the charge may be different in the final sort decision to avoid a relatively high drop charge differential.

After the preliminary sort decision has been generated, the preliminary sort decision is stored in a queue. The preliminary sort decision is then compared with other adjacent sort decisions, such as to identify any undesired drop charge sequences, such as two adjacent drops having a relatively high drop charge differential. If an undesired drop charge sequence is identified, the preliminary sort decision is modified to abort the sorting of one or more of the drops, as discussed in more detail with reference to FIG. 10. The final sort decisions comprise final electrical charges assigned to the drops which are stored in a buffer and used to generate and send the sort control signal 154 to the sort control electronics 120.

The sort decision engine also records the sort decisions in the event and status storage 164. The event and status storage 164 is, for example, a computer-readable storage device, such as those disclosed herein. The event and status storage 164 stores data about the particles identified in the fluid stream 130 and the sort decisions that were made, for example.

The sort control electronics 120 receive the sort control signal 154 from the sort decision engine 162 and operate in conjunction with the fluid nozzle 110 and oscillator 122 (shown in FIG. 2) to apply appropriate charges to drops 136 containing a particle of interest, to sort the drops and associated particles into the appropriate containers 126.

Additional details of an exemplary flow cytometer are described in more detail in U.S. Publ. No. 2008/0255705, filed on Oct. 16, 2008, and entitled "FLOW CYTOMETER SORTER," the disclosure of which is hereby incorporated by reference in its entirety. For example, this publication provides additional details about suitable acquisition electronics 114 (referred to in the publication as "acquisition electronics 108"), sort control electronics 120 (referred to as "sort control electronics 114"), event parameters computation engine 160 (referred to as "sort decision making parameter computation module 112"), and event and status storage 164 (referred to as "event and status storage 126"), as well as certain aspects of the sort decision engine 162 (referred to as "sort decision module 116") and other aspects of an exemplary flow cytometer.

Figure 4:
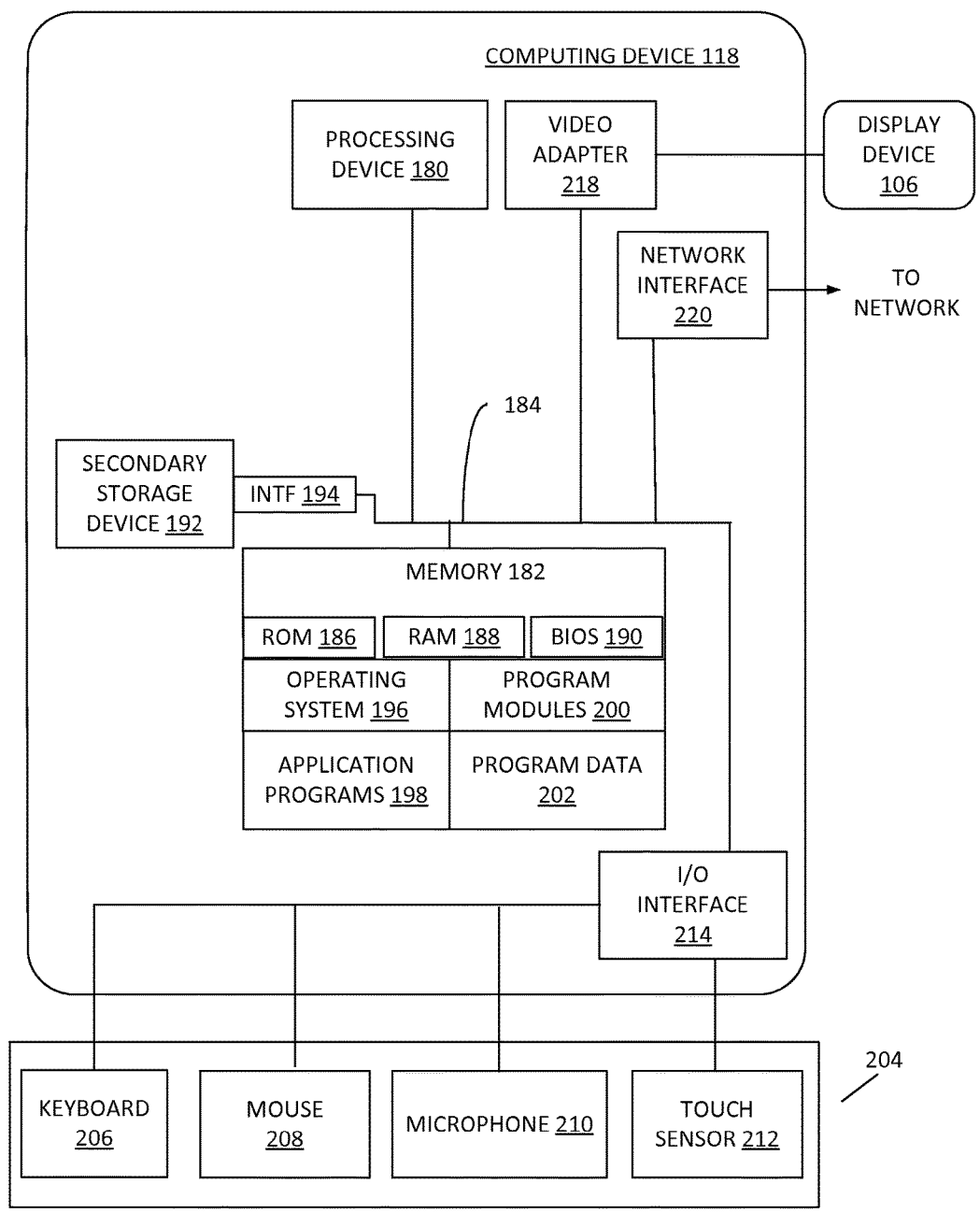
FIG. 4 illustrates an exemplary architecture of a computing device that can be used to implement aspects sorting flow cytometer.

FIG. 4 illustrates an exemplary architecture of a computing device that can be used to implement aspects of the present disclosure, including any of the one or more computing devices 118 that can be used within the sorting flow cytometer 104. The computing device illustrated in FIG. 4 can be used to execute, with the processing device 180, the operating system, application programs, and software modules (including the software engines) described herein.

The computing device 118 includes, in some embodiments, at least one processing device 180, such as a central processing unit (CPU). A variety of processing devices are available from a variety of manufacturers, for example, Intel or Advanced Micro Devices. In this example, the computing device 118 also includes a system memory 182, and a system bus 184 that couples various system components including the system memory 182 to the processing device 180. The system bus 184 is one of any number of types of bus structures including a memory bus, or memory controller; a peripheral bus; and a local bus using any of a variety of bus architectures.

Examples of computing devices suitable for the computing device 118 include a desktop computer, a laptop computer, a tablet computer, a mobile computing device (such as a smart phone, an iPod® or iPad® mobile digital device, or other mobile devices), or other devices configured to process digital instructions.

The system memory 182 includes read only memory 186 and random access memory 188. A basic input/output system 190 containing the basic routines that act to transfer information within computing device 118, such as during start up, is typically stored in the read only memory 186.

The computing device 118 also includes a secondary storage device 192 in some embodiments, such as a hard disk drive, for storing digital data. The secondary storage device 192 is connected to the system bus 184 by a secondary storage interface 194. The secondary storage devices 192 and their associated computer readable media provide nonvolatile storage of computer readable instructions (including application programs and program modules), data structures, and other data for the computing device 118.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 192 or memory 182, including an operating system 196, one or more application programs 198, other program modules 200 (such as the software engines described herein, including the event parameters computation engine 160 and sort decision engine 162), and program data 202. The computing device 118 can utilize any suitable operating system, such as Microsoft Windows™, Google Chrome™, Apple OS, and any other operating system suitable for a computing device. Other examples can include Microsoft, Google, or Apple operating systems, or any other suitable operating system used in tablet computing devices.

In some embodiments, a user provides inputs to the sorting flow cytometer 104 and the computing device 118 through one or more input devices 204. Examples of input devices 204 include a keyboard 206, mouse 208, microphone 210, and touch sensor 212 (such as a touchpad or touch sensitive display 106). Other embodiments include other input devices 204. The input devices are often connected to the processing device 180 through an input/output interface 214 that is coupled to the system bus 184. These input devices 204 can be connected by any number of input/output interfaces, such as a parallel port, serial port, game port, or a universal serial bus. Wireless communication between input devices and the interface 214 is possible as well, and includes infrared, BLUETOOTH® wireless technology, 802.11a/b/g/n, cellular, or other radio frequency or electromagnetic communication systems in some possible embodiments.

In this example embodiment, a display device 106, such as a monitor, liquid crystal display device, projector, or touch sensitive display device, is also connected to the system bus 184 via an interface, such as a video adapter 218. In addition to the display device 106, the computing device 118 can include various other peripheral devices (not shown), such as speakers or a printer.

When used in a local area networking environment or a wide area networking environment (such as the Internet), the computing device 118 is typically connected to a data communication network through a network interface 220, such as an Ethernet interface. Other possible embodiments use other communication devices. For example, some embodiments of the computing device 118 include a modem for communicating across the network.

The computing device 118 typically includes at least some form of computer readable media. Computer readable media includes any available media that can be accessed by the computing device 118. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 118.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 4 is also an example of programmable electronics, which may include one or more such computing devices, and when multiple computing devices are included, such computing devices can be coupled together with a suitable data communication network so as to collectively perform the various functions, methods, or operations disclosed herein.

Figure 5:
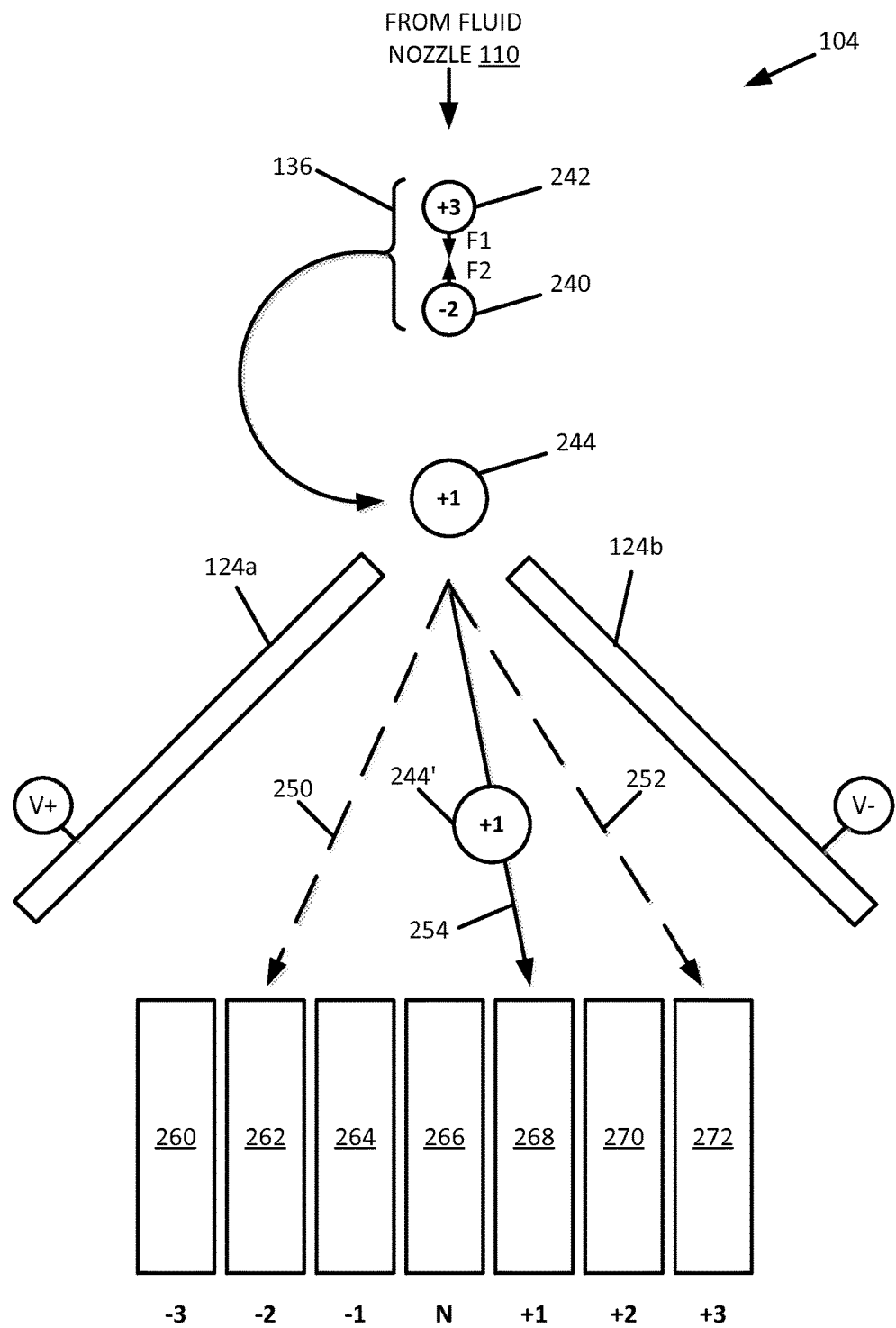
FIG. 5 is a schematic block diagram illustrating an undesirable method of operating the sorting flow cytometer.

FIG. 5 is schematic block diagram illustrating an undesirable method of operating the sorting flow cytometer 104. FIG. 5 illustrates drops 136 from the fluid nozzle 110, deflection plates 124, and containers 126. The drops 136 include two adjacent drops 240 and 242, which merge to form drop 244. The containers 126 include containers 260, 262, 264, 266, 268, 270, and 272.

In this example, the acquisition electronics have previously identified particles in two adjacent drops 240 and 242 that the sort decision engine 162 determined belonged in containers 262 and 272 respectively. Accordingly, the sort control electronics 120 applied a charge ("−2") to drop 240 to direct the drop 240 into container 262, and applied a charge ("+3") to drop 242 to direct the drop 242 into container 272.

The charge values used in this example (e.g., −2 and +3) represent the relative magnitude and polarity of the charge needed to direct a drop into a desired container on a scale from no charge (represented by 0) to a maximum charge magnitude (represented by 3).

So, for example, a charge of −3 is needed to direct a drop into container 260. A charge of −2 is needed to direct a drop into container 262. A charge of +3 is needed to direct a drop into container 272, and so on. Uncharged drops are directed into container 266 without deflection.

An undesired drop charge sequence is illustrated in FIG. 5, which includes drop 240 having a relatively high negative charge (−2), and drop 242 having a relatively high charge of the opposite polarity (+3). As a result of the opposite polarity charges on drops 240 and 242, forces are generated between the two drops tending to pull the two drops toward each other.

If the magnitudes of the forces are sufficient, as in this example, the drops 240 and 242 merge with one another forming a combined drop 244, before the drops are sorted. The charges of drops 240 and 242, being opposite in polarity, are largely canceled out, resulting in a combined charge with a lower magnitude (+1).

As a result of the union, drops 240 and 242 that were intended to be sorted into containers 262 and 272 (along paths 250 and 252), are instead directed along path 254 as a combined drop 244' into container 268.

This has two undesirable results. First, the particles within drops 240 and 242 are not collected in the appropriate containers 262 and 272. Second, the particles are incorrectly directed into container 268, thereby polluting the contents of container 268 with particles that may not have been intended to be in that container.

A similar undesirable result can occur when drops 240 and 242 are charged with the maximum charge magnitudes of opposite polarities (e.g., +3 and −3). However, in this example, when drops 240 and 242 merge to form a combined drop 244, the equal and opposite charges cancel each other out, and the combined drop 244 is directed into container 266 with the other unsorted drops. While this example does not cause pollution of the containers, it results in a reduced yield of the sorting flow cytometer 104 by failing to sort drops containing desired particles.

Figure 6:
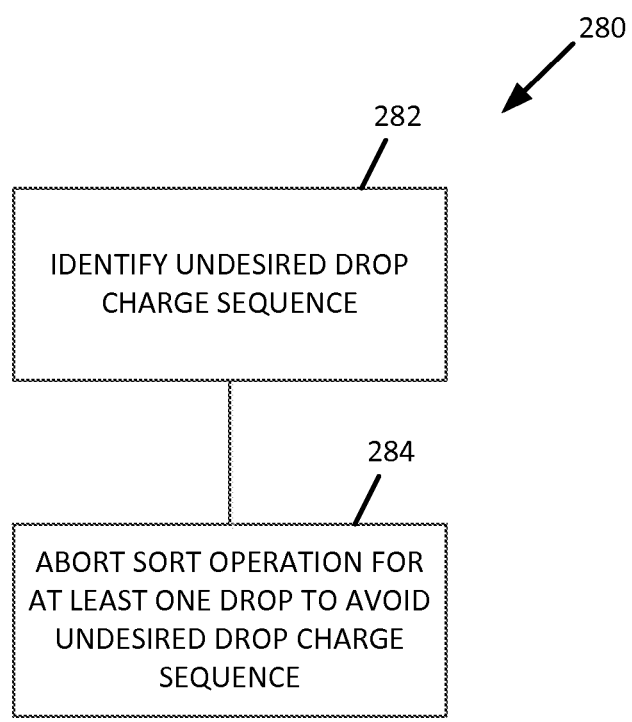
FIG. 6 is a flow chart illustrating a method of operating the flow cytometer to avoid the undesirable operation shown in FIG. 5.

FIG. 6 is a flow chart illustrating a method 280 of operating the sorting flow cytometer 104, such as to avoid the undesired operation illustrated in FIG. 5. In this example, the method 280 includes operations 282 and 284.

Operation 282 is performed to identify an undesired drop charge sequence. An example of an undesired drop charge sequence is illustrated in FIG. 5, in which two or more adjacent drops 240 and 242 have relatively high charges of opposite polarities.

In the example shown in FIG. 5, the drop charge sequence of drops 240 and 242 is undesirable because the respective charges on the drops 240 and 242 are sufficient to result in merging of the drops 240 and 242 into a single drop 244 prior to sorting.

Operation 282 can be performed, for example, by the sort decision engine 162 executed on one or more computing devices 118. An example of operation 282 is illustrated and described in more detail with reference to FIG. 8.

The identification of the undesired drop charge sequence in operation 282 is typically performed prior to application of charges to the drops, and even before the actual formation of the drops 136 themselves. As a result, references to the "drop charge sequence" refer to the preliminary sort decisions that are made after a fluid portion of fluid stream 130 (FIG. 2) has passed by the laser illumination point 132, but before the fluid portion has passed the drop break off point 134 to form a separate drop. The preliminary sort decisions are typically stored in a computer-readable storage device. In some embodiments, the computer-readable storage device maintains a queue, where each entry in the queue is associated with a given fluid portion that is expected to break off and form a separate drop. The entry in the queue includes the preliminary sort decision, which if finalized and passed as a sort control signal 154, will cause the drop to be sorted into the appropriate container 126. The preliminary sort decisions can be evaluated for adjacent drops to identify undesired drop sequences in the queue.

Figure 7:
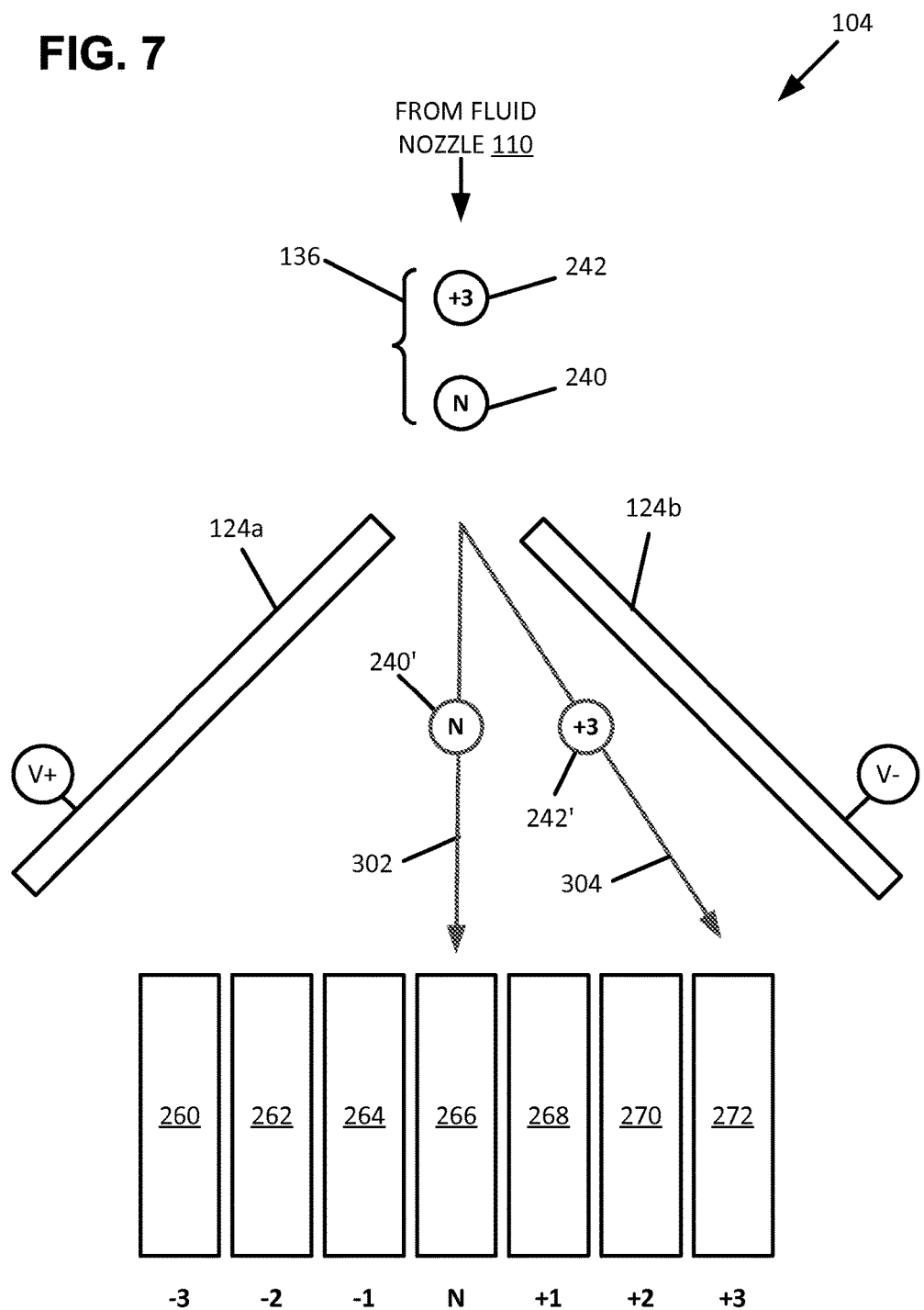
FIG. 7 is a schematic block diagram illustrating a desirable method of operating the sorting flow cytometer.

When an undesired drop charge sequence is identified, operation 284 is then performed to abort a sort operation for at least one of the drops in the sequence to avoid formation of the undesired drop charge sequence. An example is illustrated in FIG. 7. A sort operation can be aborted by assigning a neutral charge to the drop that is aborted. Additional details of an example of operation 284 are described with reference to FIG. 10.

FIG. 7 is a schematic block diagram illustrating a desirable method of operation of the sorting flow cytometer 104, utilizing the method 280, shown in FIG. 6, and in contrast to the undesirable operation illustrated in FIG. 5.

The sorting flow cytometer 104 shown in FIG. 7 is the same as shown in FIG. 5, except that the method 280 is utilized to detect the undesirable drop charge sequence before it is formed, and to abort the sort operation for one of the drops 240.

In this example, the sort decision engine 162 evaluated the preliminary sort decisions for drops 240 and 242 and identified an undesired drop charge sequence, in which the two adjacent drops were going to be charged with high opposing charges. As a result, the sort decision engine 162 modified the preliminary sort decision to abort the sorting of one of the drops 240 and 242. More specifically, the sort decision engine 162 determined to abort the sorting of drop 240. A neutral charge is assigned to the drop 240, and as a result, the drop 240 was not charged by the sort control electronics 120, but drop 242 was charged by the sort control electronics 120 according to the sort decision (+3).

As a result of the modified sort decision, uncharged drop 240' was not deflected by the deflection plates 124, and continued straight through along path 302 into container 266. On the other hand, the charged drop 242' was deflected along path 304, to properly sort the drop 242' into container 272.

The sort decision engine 162 could alternatively choose to abort the sorting of drop 242 and continue with the sorting of drop 240. In this case, drop 240 would be charged (−2) and sorted into container 262, while drop 242 remains uncharged and is passed to container 266.

Therefore, by utilizing the operations shown in FIG. 6, the sorting flow cytometer 104 is improved. For example, none of the drops 240 or 242 were delivered to an unintended container, as occurred in the example shown in FIG. 5. The purity of the sorting is therefore greatly improved by reducing or eliminating the missorting of particles into the incorrect containers. In some embodiments, the purity of the sorting is greater than or equal to 99% for each container. In addition, even though one of the drops is passed into container 266 without sorting, the sorting flow cytometer can choose which of the drops to sort, and which of the drops to pass to container 266. Oftentimes one of the drops will contain particles that are more important than the other. As a result, in some embodiments the sort decision engine 162 ranks the drops utilizing a predetermined priority to identify the more important particles and select the drop containing those particles for sorting, while allowing the drop containing the less important particles to pass into container 266.

Figure 8:
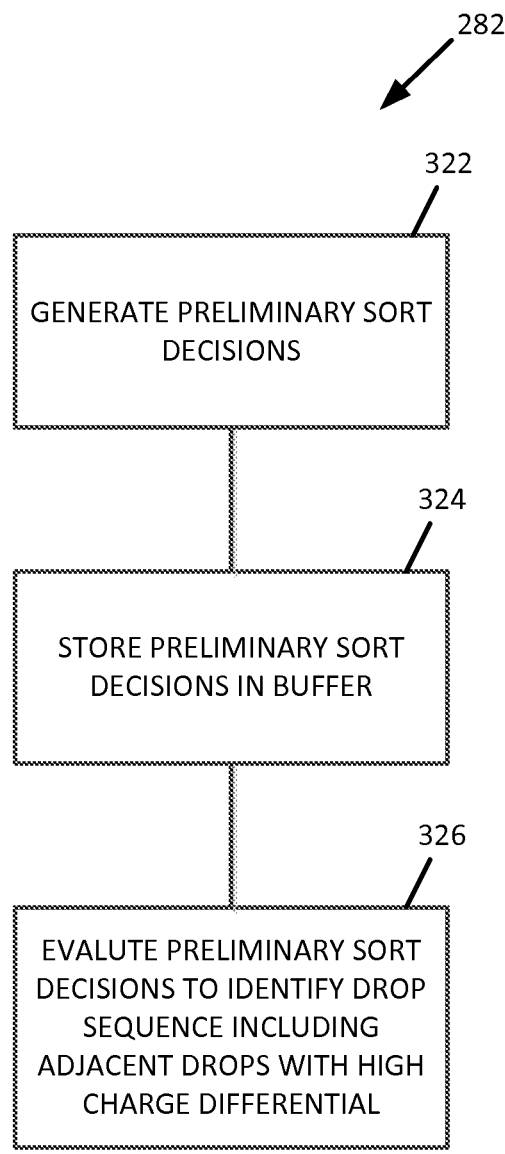
FIG. 8 illustrates an exemplary method of identifying an undesired drop charge sequence.

FIG. 8 illustrates an exemplary method of identifying an undesired drop charge sequence. The method is also an example of operation 282, shown in FIG. 6. In this example, the operation 282 includes operations 322, 324, and 326.

Operation 322 is performed to generate preliminary sort decisions. The preliminary sort decisions are made based on the particles identified in portions of the fluid stream, and the sort logic definitions which define where drops should be directed if they contain certain particles. The sort decisions are made for each portion of the fluid stream based on the predicted separation of the stream into individual drops, such that a sort decision is made for each drop.

In operation 324 the preliminary sort decisions made in operation 322 are stored in a computer readable storage device. In some embodiments, the sort decisions are stored as a queue in a buffer. An example of such a buffer is illustrated in FIG. 9. Some embodiments utilize a circular buffer. Some embodiments utilize a direct memory access (DMA) memory buffer.

Operation 326 evaluates the preliminary sort decisions to identify undesired drop charge sequences. More specifically, operation 326 evaluates the preliminary sort decisions to determine whether the sort decisions would result in a drop sequence in which adjacent drops have an unacceptably high charge differential.

In some embodiments, operation 326 utilizes a sliding window to evaluate a portion of the preliminary sort decisions at a time. The sliding window can include two, three, four, or five or more sort decisions for a corresponding number of fluid segments in the fluid stream. Operation 326 then evaluates the sort decisions within the sliding window to identify undesirable drop charge sequences.

Figure 10:
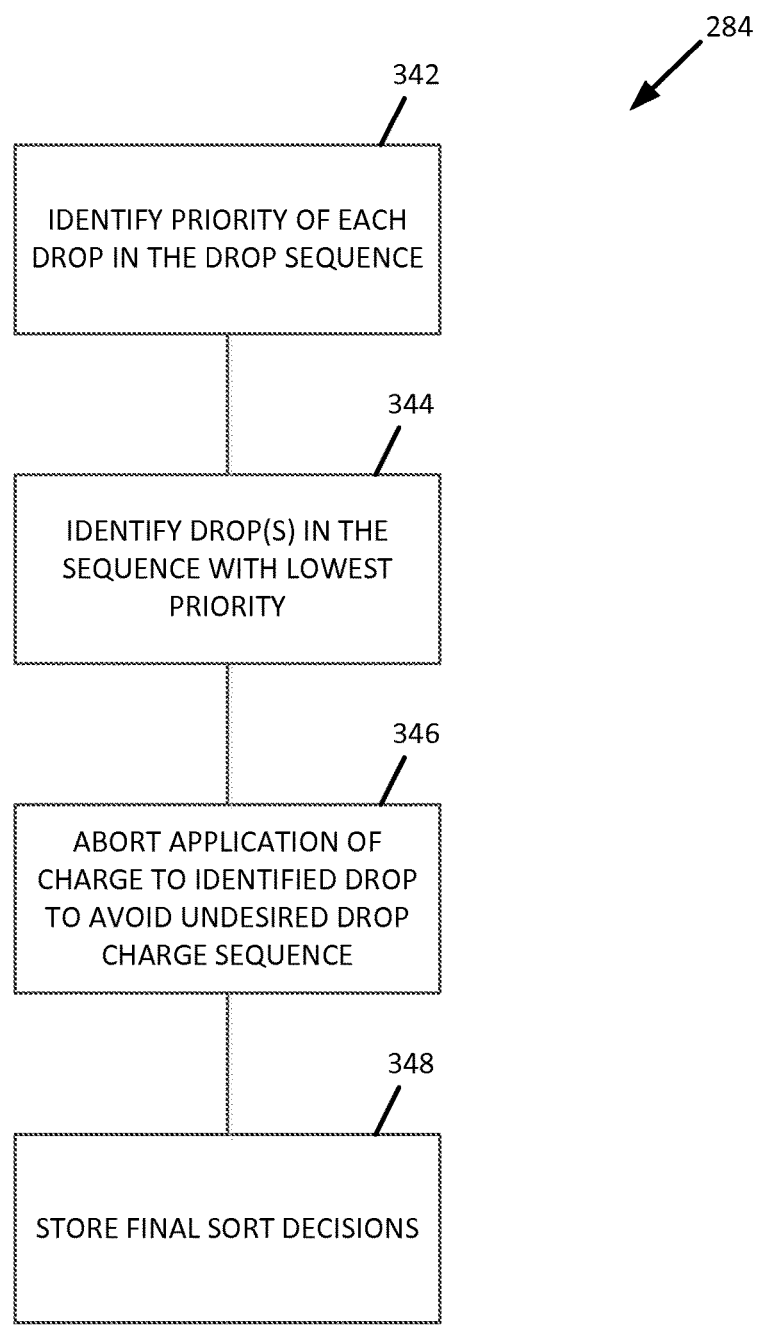
FIG. 10 illustrates an exemplary method of identifying one or more drops for which sorting should be aborted, after identifying an undesired drop charge sequence.

In some embodiments, the undesirable drop charge sequences are identified by comparing the sort decisions with a set of predetermined undesirable drop charge sequences, such as stored in a lookup table. If a match is found, the drop sequence is identified as an undesired drop charge sequence. Additional processing is then performed, such as shown in FIG. 10.

In another embodiment, undesired drop charge sequences are identified by comparing the drop charges assigned to drops with predetermined maximum deflection values. For example, each drop charge is first evaluated to determine if the drop charge exceeds a maximum deflection value. If so, adjacent drops are evaluated to determine if either of the adjacent drops exceeds a maximum opposing deflection value. If either or both of the charges assigned to the adjacent drops exceed the maximum opposing deflection value, the associated drops are identified as an undesired drop charge sequence.

In some embodiments, the drop charges are assigned a value between zero and a maximum value (e.g., 32,767), where the maximum value represents the maximum voltage that can be applied by the sort control electronics 120 for charging the fluid stream 130. Drop charges also include a polarity, such as positive or negative. The maximum deflection values are then set at a value between 0 and the maximum value. For example, a value of 19,660 can be used in some embodiments, although other embodiments utilize other values. The maximum deflection values can be adjusted based on a variety of factors, such as nozzle size, for example.

The maximum opposing deflection value is similarly assigned as a value between 0 and the maximum value. For example, a value of 8,191 can be used in some embodiments, although other embodiments utilize other values. The maximum opposing deflection values can also be adjusted based on a variety of factors, such as nozzle size, for example.

In some embodiments, the undesired drop charge sequence is identified by computing a charge differential between adjacent drops, and determining whether the charge differential exceeds a threshold.

In some embodiments, the maximum deflection value, maximum opposing deflection value, and/or the threshold are determined by testing, where the values are set so that they are exceeded when two adjacent drops have a sufficient charge differential so that they would merge if the sorting of at least one of the drops was not aborted.

In some embodiments, a computation can be performed to generate the maximum deflection values, maximum opposing deflection values, and/or other threshold values. The computation can determine the maximum deflection values at which point drops will begin to merge. The computation can include factors such as: a fluid nozzle size, a drop fall distance between a drop breakoff point and charged deflection plates, a time that it takes a drop to move the drop fall distance, drop masses, drop charge magnitudes, drop charge differentials between adjacent drops, drop charge polarities, sheath pressure, and stream velocity.

In some embodiments, the computation is automatically performed any time that a relevant factor changes, such as upon adjustment of the fluid nozzle size.

FIG. 9 is a schematic block diagram illustrating an example buffer containing preliminary sort decisions. In this example, the preliminary sort decisions identify a drop position 332 and a charge to be applied 334 to the drop according to the preliminary sort decision.

In this example, the drop position 332 identifies the position of the drop within the fluid stream 130. For example, the letter N represents the portion of the fluid segment that is next to cross the drop break off point 134 (FIG. 2). Each drop is incremented from this drop in consecutive order, such that "N+1" represents the second fluid segment, "N+2" represents the third fluid segment, etc.

The charge to be applied 334 is then stored for each drop position 332. In some embodiments the drop charge is a number between 0 and the maximum value (e.g., 32,767), which represents the maximum voltage that can be applied by the sort control electronics 120 to the fluid stream 130, and a polarity (e.g., positive or negative).

A shorthand notation is used in FIG. 9 (and elsewhere herein) for simplicity, in which the maximum value is 3, resulting in six possible charges (−3, −2, −1, +1, +2, and +3). Using this notation and referring to FIG. 7, a drop assigned a charge of −3 is intended to be directed into the most distant container 260, −2 directs to container 262, −1 directs to container 264, +1 directs to container 268, +2 directs to container 270, and +3 directs to container 272. Uncharged drops are directed to container 266.

In this example, the sort decision engine has been assigned a maximum differential value of 2 and a maximum opposing differential value of 1.

Using these values, the drops are evaluated for an undesired sort sequence. In this example, two drops, labeled N+1 and N+3 are identified that have a magnitude (3) that exceeds the maximum differential value (2). As a result, the adjacent drops are evaluated to determine if they exceed the maximum opposing differential value (1).

Drop N and N+4 have a magnitude of (1) which does not exceed the maximum opposing differential value (1). However, drop N+2 has a magnitude (2) that does exceed the maximum opposing differential value (1). Accordingly, drops N+1, N+2, and N+3 are identified as an undesired sort sequence for further processing, such as shown in FIG. 10.

FIG. 10 illustrates an exemplary method of identifying one or more drops for which sorting should be aborted, after identifying an undesired drop charge sequence. The method is also an example of operation 284, shown in FIG. 6. In this example, the operation 284 includes operations 342, 344, 346, and 348.

Operation 342 is performed to identify a priority of each drop in the drop sequence. In some embodiments, drop priorities are assigned based on the types or quantities of particles in a drop. The drop priorities can be selected by the user in some embodiments.

In some embodiments, drops are associated with one of several drop modes based on the particles contained in the drop. Examples of the drop modes include single mode, purify mode, and an enrich mode. A single mode drop is a drop that contains only a single particle. A purify mode drop is one that contains one or more particles of a single type. An enrich mode drop is one that contains an important particle, but may also contain other particles of other types. In some embodiments, the priorities are assigned based on the drop mode, where single is the highest priority, purify has a lower priority, and enrich has the lowest priority.

In another possible embodiment, priorities are assigned based on container positions, where the outer containers have a higher priority than the inner containers. In the case of a tie, containers on the left side can be given a higher priority than containers on the right side, or vice versa.

In some embodiments, values are assigned to each priority level, such as 1 to 3, where 3 is the lowest priority. Other values can also be used in other embodiments.

In some embodiments, the priorities are stored in the buffer 330 along with the drop preliminary sort decisions. An example is illustrated in FIG. 11.

Operation 344 is performed to identify one or more drops in the undesired drop charge sequence having the lowest priority.

Operation 346 aborts the application of a charge to the one or more drops in the sequence that have the lowest priorities.

The final sort decisions are stored in a computer readable storage device in operation 348, such as in the same or another buffer, to generate the sort control signal 154 (FIG. 3). An example is illustrated in FIG. 12.

As a result of these decisions, the final sorting decision causes the sorting flow cytometer to selectively not apply the preassigned charge to one of the drops, while applying the other preassigned charges (which become the final sort decisions) to the other drops that are not aborted.

FIG. 11 is a schematic block diagram illustrating another example buffer 330', similar to that shown in FIG. 9, but also containing priority data 352.

In this example, each of the drops identified in the buffer 330' includes a position number 332, a charge to be applied 334, and a priority 352.

After identifying an undesired drop charge sequence, as shown, the priorities of the drops in the sequence are identified and evaluated. In this example, drop N+1 has a priority of 1 (high), drop N+2 has a priority of 2 (medium), and drop N+3 has a priority of 1 (high). Accordingly, drop N+2 is determined to have the lowest priority.

Once the drop(s) having the lowest priority have been identified, the sorting of the associated drop(s) is aborted. So, in this example, the sorting of drop N+2 is aborted. The final sort decisions are then generated as shown in FIG. 12.

In another possible embodiment, sort decisions include primary sort decisions and secondary sort decisions. The decisions discussed above are examples of primary sort decisions. A drop can also be assigned a secondary sort decision. In the event that a primary sort decision must be aborted, the drop can be assigned a secondary sort decision. The evaluation of the sort decision is then repeated to determine whether the secondary sort decision would still result in an undesired drop charge sequence, or whether the secondary sort decision eliminates the undesired drop charge sequence. If the secondary sort decision resolves the issue, sorting of the drop is allowed to proceed according to the secondary decision. If the secondary sort decision continues to result in an undesired drop charge sequence, the sorting of one or more drops having the lowest priority are aborted.

FIG. 12 is a schematic block diagram illustrating an example buffer 362 in which the preliminary sort decisions (shown in FIGS. 9 and 11) are modified to abort the sorting operation for one or more drops in order to avoid the formation of an undesired drop charge sequence. More specifically, the charge assigned to drop N+2 has been changed so that a charge will not be applied to this drop. By aborting the sorting of drop N+2, the sorting for drops N+1 and N+3 can proceed to direct the high priority drops into the appropriate containers.

Table 1 illustrates some additional examples of possible drop sequences, and the associated decisions that can be made to abort one or more drops. An asterisk represents a drop that is part of an undesired drop sequence. The number in parenthesis followed by the letter "P" indicates the drop priority.

| Sequence | Drop N Charge | Drop N + 1 Charge | Drop N + 2 Charge | Drop N + 3 Charge | Drop N + 4 Charge | Drops Aborted |
|---|---|---|---|---|---|---|
| 1 | −1 | −3* (P1) | +2* (P2) | −1 | 0 | N + 2 |
| 2 | −1 | −3* (P2) | +2* (P1) | −1 | 0 | N + 1 |
| 3 | −1 | +2* (P1) | −3* (P2) | −1 | 0 | N + 2 |
| 4 | −1 | +2* (P2) | −3* (P1) | −1 | 0 | N + 1 |
| 5 | −1 | −3* (P1) | +2* (P2) | −3* (P1) | 0 | N + 2 |
| 6 | −1 | −3* (P2) | +2* (P1) | −3* (P2) | 0 | N + 1 and N + 3 |
| 7 | −1 | +2* (P1) | −3* (P2) | +2* (P1) | 0 | N + 2 |
| 8 | −1 | +2* (P2) | −3* (P1) | +2* (P2) | 0 | N + 1 and N + 3 |
| 9 | −1 | +2* (P3) | −3* (P2) | +2* (P1) | 0 | N + 2 |

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A sorting flow cytometer comprising:
   a fluid nozzle configured to receive a fluid input and generate a fluid stream along a fluid path;
   a laser configured to generate a laser beam and positioned to direct the laser beam at the fluid stream;
   acquisition electronics including a sensor analyzer arranged and configured to detect light from the laser after the laser beam has intersected the fluid stream;
   a computing device in data communication with the acquisition electronics;
   a computer readable data storage device storing data instructions that, when executed by the computing device, cause the computing device to perform the following steps:
     identify segments of the fluid stream, including a first segment and a second segment that are directly adjacent to each other;
     generate preliminary sort decisions that assign preliminary charges to segments of the fluid stream including a first preliminary sort decision that assigns a first preliminary charge to the first segment and a second preliminary sort decision that assigns a second preliminary charge to the second segment;
     evaluate the first preliminary sort decision and the second preliminary sort decision;
     generate final sort decisions that include a modification to the first preliminary sort decision or the second preliminary sort decision to assign a neutral charge for at least one of the first segment or the second segment; and
     generate a sort control signal according to the final sort decisions;
   sort control electronics in data communication with the computing device, configured to receive the sort control signal from the computing device and selectively apply charges to the segments of the fluid stream prior to a drop break off point; and
   deflection plates arranged adjacent to the fluid path to sort drops formed from the segments of the fluid stream into a plurality of containers.

2. The sorting flow cytometer of claim 1, wherein the computer readable data storage device stores data instructions that, when executed by the computing device, cause the computing device to determine if a sequence of preliminary charges assigned to adjacent segments of the fluid stream matches a sequence of charges in a lookup table.

3. The sorting flow cytometer of claim 1,
wherein said sorting flow cytometer is a six-way sorting cytometer,
wherein the preliminary sort decisions are associated with relative charges of +/−a, +/−b, or +/−c, wherein a, b, and c represent magnitudes, a<b<c, and +/− represent polarities; and
wherein the computer readable data storage device stores data instructions that, when executed by the computing device, cause the computing device to generate final sort decisions by modifying the preliminary sort decisions to assign a neutral charge for at least one of the adjacent segments of the fluid stream if the combination of preliminary charges is one of +c and −b; +c and −c; and +b and −c.

4. The sorting flow cytometer of claim 1, wherein the computer readable data storage device stores data instructions that, when executed by the computing device, cause the computing device to determine whether adjacent segments of the fluid stream are assigned preliminary charges of opposite polarities that exceed a predetermined threshold value.

5. The sorting flow cytometer of claim 1, wherein the computer readable data storage device stores data instructions that, when executed by the computing device, cause the computing device to calculate the differential between preliminary charges assigned to adjacent segments of the fluid stream.

6. The sorting flow cytometer of claim 1, wherein the computer readable data storage device stores data instructions that, when executed by the computing device, cause the computing device to evaluate the preliminary sort decisions of adjacent segments of the fluid stream by utilizing a sliding window to evaluate a portion of the preliminary sort decisions at a time.

7. The sorting flow cytometer of claim 1, wherein the final sort decision is based on the relative locations of the containers within the plurality of containers.

* * * * *